(12) United States Patent
Vorarath

(10) Patent No.: US 11,360,064 B2
(45) Date of Patent: Jun. 14, 2022

(54) OXY-PYROHYDROLYSIS SYSTEM AND METHOD FOR TOTAL HALOGEN ANALYSIS

(71) Applicant: 3M INNOVATIVE PROPERTIES COMPANY, St. Paul, MN (US)

(72) Inventor: Phanasouk Vorarath, Cottage Grove, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 745 days.

(21) Appl. No.: 16/089,028

(22) PCT Filed: Mar. 17, 2017

(86) PCT No.: PCT/US2017/022990
§ 371 (c)(1),
(2) Date: Sep. 27, 2018

(87) PCT Pub. No.: WO2017/172390
PCT Pub. Date: Oct. 5, 2017

(65) Prior Publication Data
US 2020/0300824 A1    Sep. 24, 2020

Related U.S. Application Data

(60) Provisional application No. 62/371,034, filed on Aug. 4, 2016, provisional application No. 62/315,413, filed on Mar. 30, 2016.

(51) Int. Cl.
*G01N 31/12* (2006.01)
*G01N 33/00* (2006.01)
*F23M 20/00* (2014.01)

(52) U.S. Cl.
CPC ............ *G01N 31/12* (2013.01); *F23M 20/00* (2015.01); *G01N 33/0049* (2013.01)

(58) Field of Classification Search
CPC ..... G01N 31/12; G01N 33/0049; F23M 20/00
(Continued)

(56) References Cited

U.S. PATENT DOCUMENTS 2,207,193 A * 7/1940 Groll ....................... C07C 17/25
570/226
2,584,969 A * 2/1952 Chapman ................ C07C 13/20
585/357
(Continued)

FOREIGN PATENT DOCUMENTS

DE        10028391      * 12/2001
FR         2525752      * 10/1983
(Continued)

OTHER PUBLICATIONS

Folestad, S. et al, Analytical Chemistry 1987, 59, 334-339.*
(Continued)

*Primary Examiner* — Arlen Soderquist
(74) *Attorney, Agent, or Firm* — Yufeng Dong

(57) ABSTRACT

Oxy-pyrohydrolysis articles, systems and methods for total halogen, in particular fluorine analysis are provided. A sample containing halogen elements is provided into a pyrotube for combustion. A combustion-enhancing bed including ceramic fibers or fabrics is disposed inside the pyrotube to enhance the combustion and protect the pyrotube from damage by corrosive gases.

18 Claims, 5 Drawing Sheets

(58) Field of Classification Search
USPC ..... 422/78, 80; 436/124, 126, 155, 159–160
See application file for complete search history.

(56) References Cited

U.S. PATENT DOCUMENTS

| | | | | |
|---|---|---|---|---|
| 2,610,893 | A | * | 9/1952 | Collins ................. F24F 6/04 442/417 |
| 2,831,906 | A | * | 4/1958 | Winberg ............... C07C 1/30 585/353 |
| 2,926,747 | A | * | 3/1960 | Wright ................. F24F 8/10 96/121 |
| 3,001,917 | A | * | 9/1961 | Scheirer .............. G01N 31/12 205/779.5 |
| 3,033,193 | A | * | 5/1962 | Rathman ............... F24F 6/04 126/113 |
| 3,090,179 | A | * | 5/1963 | Powell ............ F02M 25/0225 96/294 |
| 3,094,479 | A | * | 6/1963 | Sweeney ............... C07C 2/78 208/176 |
| 3,185,743 | A | * | 5/1965 | La Combe ........... C07C 69/533 585/638 |
| 3,235,336 | A | * | 2/1966 | Matsuyama .......... G01N 33/84 436/125 |
| 3,346,246 | A | * | 10/1967 | Loetel .................. F28C 1/00 261/103 |
| 3,423,966 | A | * | 1/1969 | Mitchell ............... D06F 75/30 68/222 |
| 3,544,084 | A | * | 12/1970 | Macrow ............... B01D 47/16 261/29 |
| 3,565,583 | A | * | 2/1971 | McNulty ............. G01N 31/002 436/114 |
| 3,795,524 | A | | 3/1971 | Sowman |
| 3,636,178 | A | * | 1/1972 | Frank .................. C07C 5/387 585/404 |
| 3,703,355 | A | * | 11/1972 | Takahashi ............ G01N 31/12 436/113 |
| 3,748,828 | A | * | 7/1973 | Lefebvre ........... B01F 3/04475 95/64 |
| 3,771,962 | A | * | 11/1973 | Winterhalter ...... G01N 33/1846 422/80 |
| 3,895,068 | A | * | 7/1975 | Duling ................ C07C 45/512 568/354 |
| 4,047,965 | A | | 9/1977 | Karst |
| 4,054,414 | A | * | 10/1977 | Grob .................. G01N 30/66 436/115 |
| 4,234,315 | A | * | 11/1980 | Scott .................. G01N 30/12 422/78 |
| 4,285,699 | A | | 8/1981 | Itoh |
| 4,330,298 | A | * | 5/1982 | Hawn ................. G01N 27/42 205/786.5 |
| 4,401,763 | A | | 8/1983 | Itoh |
| 4,419,302 | A | * | 12/1983 | Nishino ............... F22B 1/284 122/487 |
| 5,064,617 | A | | 11/1991 | O'Brien |
| 5,167,795 | A | * | 12/1992 | Gartside ............. C10G 11/18 208/113 |
| 5,246,667 | A | | 9/1993 | Hemzy |
| 5,841,011 | A | * | 11/1998 | Hashimoto ........... C10G 1/002 585/241 |
| 5,866,072 | A | * | 2/1999 | Bowe, Jr. ............ G01N 31/12 422/78 |
| 6,474,628 | B1 | * | 11/2002 | Stroh .................. F24F 6/04 261/107 |
| 7,219,628 | B1 | * | 5/2007 | Krishnamurthy ... F28D 15/0233 122/336 |
| 7,332,541 | B2 | * | 2/2008 | Schindler ............ C08G 18/10 524/588 |
| 7,452,392 | B2 | | 11/2008 | Nick |
| 7,943,808 | B2 | * | 5/2011 | Hershkowitz ........... C01B 3/46 585/539 |
| 8,163,170 | B2 | | 4/2012 | Van Egmond |
| 9,707,536 | B2 | * | 7/2017 | Chun .................. B32B 18/00 |
| 2003/0127361 | A1 | | 7/2003 | Chae |
| 2003/0175201 | A1 | * | 9/2003 | Klett .................. C04B 38/00 423/448 |
| 2004/0126729 | A1 | * | 7/2004 | Hayashi .............. G01N 31/12 432/66 |
| 2004/0186335 | A1 | * | 9/2004 | Chae .................. C10G 9/18 585/648 |
| 2005/0019623 | A1 | * | 1/2005 | Shoji .................. B01F 5/0682 48/198.7 |
| 2008/0226525 | A1 | * | 9/2008 | Jamal ................ C01B 17/167 423/230 |
| 2010/0122564 | A1 | * | 5/2010 | Crosson .............. B01B 1/005 73/1.03 |
| 2013/0284169 | A1 | * | 10/2013 | Foote .................. A61M 16/16 128/203.14 |

FOREIGN PATENT DOCUMENTS

| | | | |
|---|---|---|---|
| GB | 1115495 | * | 5/1968 |
| WO | 01/46683 | * | 6/2001 |

OTHER PUBLICATIONS

Coute, N. et al, Applied Catalysis B: Environmental 1998, 19, 175-187.*
Domke, S. B. et al, Industrial & Engineering Chemistry Research 2001, 40, 5878-5884.*
Towfighi, J. et al, Industrial & Engineering Chemistry Research 2002, 41, 1419-1424.*
Williams, P. T. et al, Fuel, 2002, 81, 2425-2434.*
Zhu, Y. et al, Reaction Kinetics, Mechanisms, and Catalysis 2015, 116, 433-450.*
Whitehead, D. et al, Analytical Chemistry 1985, 57, 2421-2423.*
Salakhov, I. I. et al, Chemistry and Technology of Fuels and Oils 2005, 41, 386-394.*
Giudicianni, P. et al, Process and Technologies for a Sustainable Energy 2010, 8 pages.*
Kantarelis, E. et al, Energy & Fuels 2010, 24, 6142-6150.*
Hapazari, I. et al, Tanzania Journal of Science 2011, 37, 120-128.*
Alkhatib, M. F. et al, Environmentalist 2011, 31, 349-357.*
Antes, F. G. et al, Microchemical Journal 2012, 101, 54-58.*
Ruengvilairat, P. et al, Journal of Sustainable Bioenergy Systems, 2012, 2, 75-85.*
Giudicianni, P. et al, Journal of Analytical and Applied Pyrolysis 2013, 100, 213-222.*
Ragucci, R. et al, Fuel 2013, 107, 122-130.*
Kumagai, S. et al, RSC Advances 2015, 5, 61828-61837.*
Hofmann, N. R. et al, Analytical Letters 2016, 49, 1903-1916.*
International Search report for PCT International application No. PCT/US2017/022990 dated Jun. 7, 2017, 3 pages.

* cited by examiner

OXY-PYROHYDROLYSIS SYSTEM AND METHOD FOR TOTAL HALOGEN ANALYSIS

CROSS REFERENCE TO RELATED APPLICATIONS

This application is a national stage filing under 35 U.S.C. 371 of PCT/US2017/022990, filed Mar. 17, 2017, which claims the benefit of U.S. Application No. 62/315,413 filed Mar. 30, 2016, and U.S. Application No. 62/371,034, filed Aug. 4, 2016, the disclosure of which is incorporated by reference in its/their entirety herein.

TECHNICAL FIELD

The present disclosure relates to oxy-pyrohydrolysis articles or systems and methods for total halogen analysis, in particular, for fluorine content analysis in various samples.

BACKGROUND

Commercial analytical combustion systems are available and target for halogens. Various samples containing halogens can be combusted inside a pyrotube placed inside a furnace. Combustion products (e.g., gases) can be analyzed to determine the contents of halogens in the samples. Various analytical techniques for determining element contents in samples are described in, for example, U.S. Pat. Nos. 4,401,763 and 4,285,699.

SUMMARY

Briefly, in one aspect, the present disclosure describes an article including a pyrotube including one or more fluid inlets configured to direct one or more combustion ingredients into the pyrotube, and a combustion-enhancing bed being disposed inside the pyrotube. The combustion-enhancing bed includes one or more packs of ceramic fibers or fabrics.

In one aspect, the present disclosure describes an oxy-pyrohydrolysis system including a pyrotube extending along an axis thereof between a first end and a second end opposite the first end. One or more fluid inlets are located at the first end of the pyrotube and configured to direct one or more combustion ingredients into the pyrotube. A combustion-enhancing bed is disposed inside the pyrotube adjacent to the second end and includes one or more packs of ceramic fibers or fabrics. A condenser is positioned downstream of the second end of the pyrotube, and configured to condense combustion products received from the pyrotube.

In another aspect, the present disclosure describes a method including providing one or more combustion ingredients and a sample containing one or more halogen elements into a pyrotube from a first end thereof. The pyrotube extends along an axis thereof between the first end and a second end opposite the first end. A combustion-enhancing bed is disposed inside the pyrotube adjacent to the second end and includes one or more packs of ceramic fibers or fabrics. The method further includes combusting the sample inside the pyrotube to produce combustion products. In some embodiments, the method further includes condensing the combustion products by a condenser, and analyzing the combustion products to determine the respective contents of the one or more halogen elements. In some embodiments, the method is provided for fluorine analysis.

Various unexpected results and advantages are obtained in exemplary embodiments of the disclosure. One such advantage of exemplary embodiments of the present disclosure is that oxy-pyrohydrolysis articles, systems and methods described herein are capable of burning different type of samples (e.g., solids, liquids, emulsions, gases, etc.) containing fluorochemicals. The samples can be combusted without black soot formation, hence closer to 100% recovery of halogens, especially fluorine. Also, the oxy-pyrohydrolysis articles, systems and methods described herein allow continuous total halogen analysis for liquid samples (e.g., drinking water) containing analyte (e.g., fluorochemicals) in a wide range of concentrations (e.g., from about 10 ppb or lower to about 10,000 ppm or higher).

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which:

FIG. 2C' is a cross-sectional view of the oxy-pyrohydrolysis reactor of FIG. 2C along a line 2C'-2C'.

Figure 1:
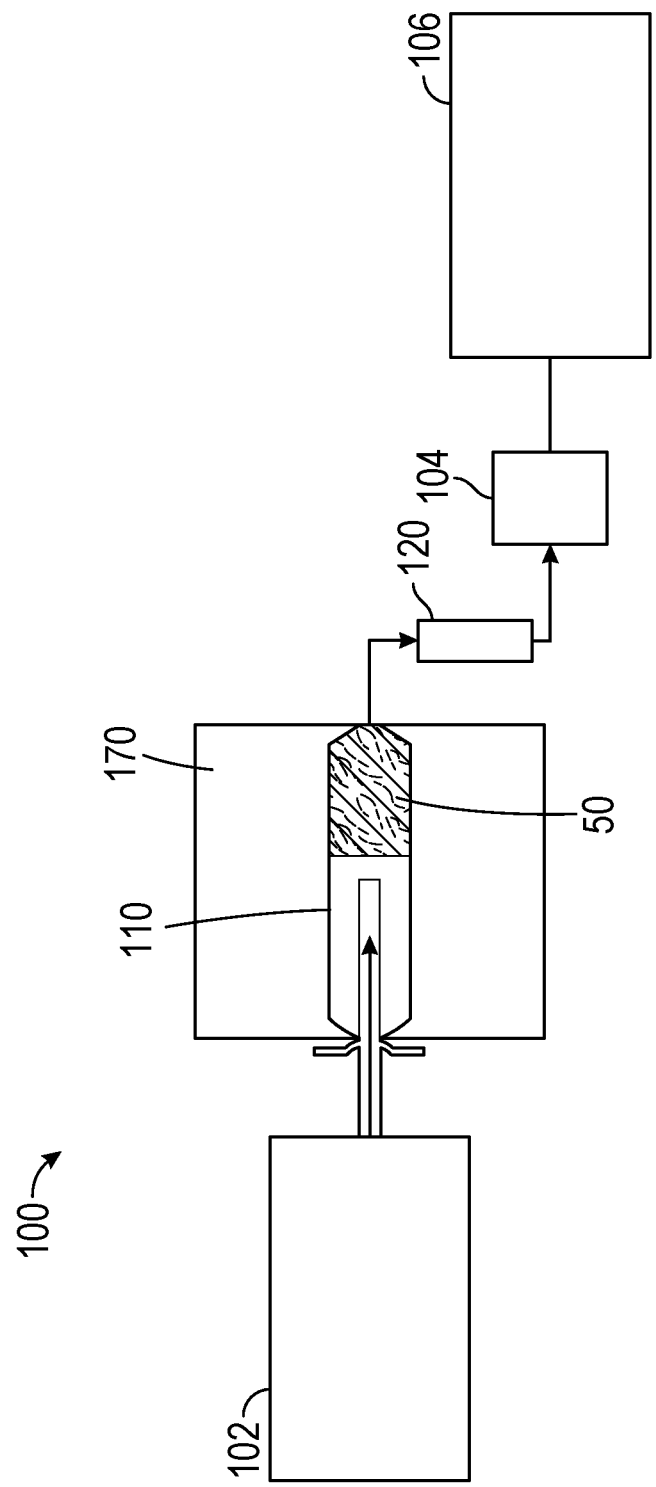
FIG. 1 is a schematic diagram of a system for analyzing total halogen content, according to one embodiment.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should understood that:

The term "oxy-pyrohydrolysis" refers to a combustion process where samples (e.g., solid, liquid, emulsion, gas, etc.) are burned into gases under the condition of combustion ingredients (e.g., water, oxygen, etc.) and heat.

The term "ceramic fabric" refers to a network of natural or artificial ceramic fibers.

By using terms of orientation such as "atop", "on", "upper", "bottom", "below", "under", and the like for the location of various elements in the disclosed systems, we refer to the relative position of the elements. However, unless otherwise indicated, it is not intended that the elements should have any particular orientation in space during or after manufacture.

The terms "about" or "approximately" with reference to a numerical value or a shape means+/−five percent of the numerical value or property or characteristic, but expressly includes the exact numerical value. For example, a viscosity of "about" 1 Pa-sec refers to a viscosity from 0.95 to 1.05 Pa-sec, but also expressly includes a viscosity of exactly 1 Pa-sec. Similarly, a perimeter that is "substantially square" is intended to describe a geometric shape having four lateral edges in which each lateral edge has a length which is from 95% to 105% of the length of any other lateral edge, but which also includes a geometric shape in which each lateral edge has exactly the same length.

The term "substantially" with reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

As used in this specification and the appended embodiments, the singular forms "a", "an", and "the" include plural referents unless the content clearly dictates otherwise. Thus, for example, reference to fine fibers containing "a compound" includes a mixture of two or more compounds. As used in this specification and the appended embodiments, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

FIG. 1 is a schematic diagram of a system 100 for analyzing a total halogen content in samples, according to one embodiment of the present disclosure. Test samples (e.g., solids, liquids, emulsions, gases, etc.) can be introduced, via a sample introduction module 102 into an oxy-pyrohydrolysis reactor 110 which can be, for example, a quartz pyrotube. In some embodiments, the sample introduction module 102 may include a boat carrier, and a known weight of test portion of a sample can be carried by the boat carrier at a controlled rate into the oxy-pyrohydrolysis reactor 110. In some embodiments, the sample introduction module 102 may include liquid delivery instrument such as, for example, a pump, an injector, etc., for continuously delivering liquid samples into the oxy-pyrohydrolysis reactor 110. The oxy-pyrohydrolysis reactor 110 is placed inside a furnace set 170 which operates at high temperatures (e.g., 1000° C. to 1100° C.). Combustion ingredients (e.g., oxygen and/or water) can be provided into the oxy-pyrohydrolysis reactor 110 for burning the test samples at high temperatures. Under such oxy-pyrohydrolysis conditions (e.g., water, oxygen, heat, etc), halogen elements (e.g., Cl, Br, fluorine, etc.) contained in the test sample can be converted into combustion products including gaseous compounds such as, for example, fluoride. The combustion products can be trapped in a condensed steam or buffer inside a condenser 120. In some embodiments, liquid water containing halogen ions (e.g., fluoride ions) can be separated from gases at the condenser 120 before it gets transferred, via a pump 104, to a fluoride meter module 106 (e.g., anion chromatograph or ion selective electrode), where the total content of halogen elements (e.g., fluorine) can be analyzed. In some embodiments, the system 100 can analyze the total fluorine content in a sample that is in the range, for example, from about 0.005 wt % to about 35 wt %. The fluoride meter module 106 is known in the field and commercially available.

In the present disclosure, a combustion-enhancing bed 50 is provided inside the oxy-pyrohydrolysis reactor 110 adjacent to a downstream end thereof. The combustion-enhancing bed 50 described herein includes one or more packs of ceramic fibers or fabrics which can effectively enhance the combustion of samples inside the reactor 110. In some embodiments, the ceramic fibers or fabrics can include, for example, alumina-based inorganic oxide fibers or fabrics. In some embodiments, the alumina-based inorganic oxide fibers or fabrics can include, for example, at least 60% by weight of alumina. In some embodiment, the alumina-based inorganic oxide fibers or fabrics can include alpha alumina. In some embodiments, the alumina-based inorganic oxide fibers or fabrics can further include silicon oxide, boron oxide, etc.

In some embodiments, the one or more packs of ceramic fibers or fabrics can occupy, for example, at least 1/10, at least about 1/8, or at least 1/4 of the length of oxy-pyrohydrolysis reactor 110 that is positioned inside the furnace set 170. In some embodiments, the one or more packs of ceramic fibers or fabrics can occupy, for example, no greater than 95%, no greater than 75%, or no greater than 50% of the length of oxy-pyrohydrolysis reactor 110 that is positioned inside the furnace set 170.

Figure 2A:
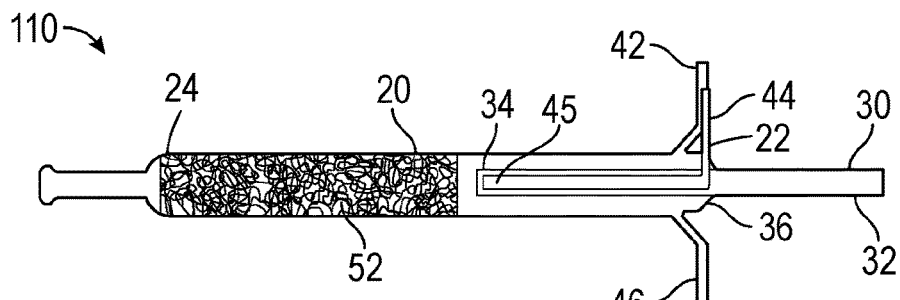
FIG. 2A is a perspective view of an oxy-pyrohydrolysis reactor of the system of FIG. 1, according to one embodiment.
Figure 2B:
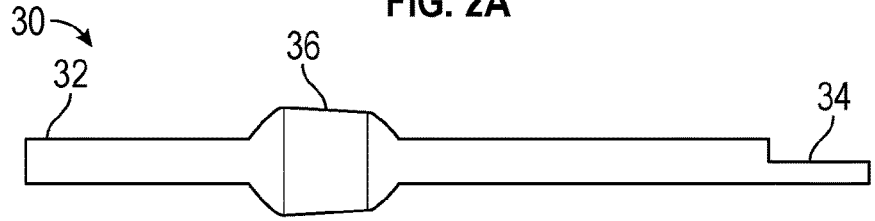
FIG. 2B is a cross-sectional view of an insert portion of the pyrotube of FIG. 2A.

FIGS. 2A-H illustrate the oxy-pyrohydrolysis reactor 110 and its components, according to various embodiments. Referring to FIG. 2A, the oxy-pyrohydrolysis reactor 110 includes a pyrotube 20 extending along an axis thereof between a first end 22 and a second end 24 opposite the first end 22 and defining a combustion chamber. The pyrotube 20 can be made of, for example, quartz, glass, ceramics, metals such as platinum that can withstand high temperatures (e.g., about 1100° C. or higher). The pyrotube 20 can have an internal diameter of, for example, about 10 mm to about 10 cm, and a length of, for example, about 10 cm to about 100 cm.

Fluid inlets 42 and 46 are located at the first end 22 of the pyrotube 20 and configured to direct combustion ingredients such as, for example, oxygen and water into the tube body 20, respectively. It is to be understood that one or more of the combustion ingredients may be optional. For example, for liquid samples such as drink water to be tested, water may not be provided from the fluid inlet 42 or 46 as one of the combustion ingredients. An optional flame sensor rod 44 is inserted into the first end 22 of the pyrotube 20 and has a distal end 45. A flame sensor (not shown) can be functionally connected to the flame sensor rod 44 to measure the intensity of light inside the pyrotube 20. It is to be understood that the flame sensor and its associated structures (e.g., the rod 44) may be optional for some liquid samples where the combustion may not generate flames. A sample insert 30 that extends between ends 32 and 34 thereof is connected to the first end 22 of the pyrotube 20 at a junction 36. In the depicted embodiment, the sample inlet 30 is a separate tube (see FIG. 2B) removably sealed to the pyrotube 20 at the junction 36. In some embodiments, the sample insert 30 can be an integral portion of the pyrotube 20. In some embodiments, the sample insert 30 may have respective desirable structures according to the different type of samples (e.g., solids, liquids, emulsions, gases, etc.) to be delivered.

In the depicted embodiment of FIG. 2A, a combustion-enhancing bed includes a pack of ceramic fibers 52 that is disposed inside the pyrotube 20 and downstream of the end 34 of the sample insert 30. The ceramic fibers 52 includes strings of ceramic fibers that are randomly rolled and packed inside the pyrotube 20. The packing density of the ceramic fibers 52 can be suitable to allow combustion gases and steam vapor to pass through. The pack of ceramic fibers 52 include one or more strings of ceramic fibers. A single string of ceramic fiber may have a length, for example, no less than one time, two times, five times, or ten times of the inner diameter of the pyrotube 20. In some embodiments, the ceramic fibers 52 can include, for example, alumina-based inorganic oxide fibers. The alumina-based inorganic oxide fibers typically have an average effective fiber diameter of at least about 5 micrometers, although this is not a requirement. In some embodiments, the average effective fiber diameter is less than or equal to 50 micrometers or less than or equal to 25 micrometers.

Useful alumina-based inorganic oxide fibers include, for example, aluminoborosilicate fibers as described in U.S. Pat. No. 3,795,524 (Sowman). In some embodiments, the aluminoborosilicate fibers comprise, on a theoretical oxide basis: about 35 percent by weight to about 75 percent by weight (more preferably, about 55 percent by weight to about 75 percent by weight) of $Al_2O_3$; greater than 0 percent by weight (more preferably, at least about 15 percent by weight) and less than about 50 percent by weight (more preferably, less than about 45 percent, and most preferably, less than about 40 percent) of $SiO_2$; and greater than about 1 percent by weight (more preferably, less than about 25 percent by weight, even more preferably, about 1 percent by weight to about 20 percent by weight, and most preferably, about 2 percent by weight to about 15 percent by weight) of $B_2O_3$, based on the total weight of the aluminoborosilicate fibers. Preferred aluminoborosilicate fibers are commercially available as NEXTEL 312 inorganic oxide fiber from 3M Company, Maplewood, Minn.

Useful alumina-based inorganic oxide fibers also include aluminosilicate fibers. Aluminosilicate fibers, which are typically crystalline, comprise aluminum oxide in the range from about 67 to about 97 percent by weight and silicon oxide in the range from about 3 to about 33 percent by weight. Aluminosilicate fibers can be made as disclosed, for example, in U.S. Pat. No. 4,047,965 (Karst et al.). In some embodiments, the aluminosilicate fibers include, on a theoretical oxide basis, from about 67 to about 85 percent by weight of $Al_2O_3$ and from about 33 to about 15 percent by weight of $SiO_2$, based on the total weight of the aluminosilicate fibers. In some embodiments, the aluminosilicate fibers include, on a theoretical oxide basis, from about 67 to about 77 percent by weight of $Al_2O_3$ and from about 23 to about 33 percent by weight of $SiO_2$, based on the total weight of the aluminosilicate fibers. In some embodiments, the aluminosilicate fiber includes, on a theoretical oxide basis, from about 85 to about 97 percent by weight of $Al_2O_3$ and from about 3 to about 15 percent by weight of $SiO_2$, based on the total weight of the aluminosilicate fibers. Aluminosilicate fibers are commercially available, for example, as NEXTEL 550 and NEXTEL 720 aluminosilicate fiber from 3M Company.

In some embodiments, the alumina fibers include, on a theoretical oxide basis, greater than about 98 percent by weight of $Al_2O_3$ and from about 0.2 to about 1.0 percent by weight of $SiO_2$, based on the total weight of the alumina fibers. Alpha alumina fibers are available, for example, as NEXTEL 610 inorganic oxide fiber from the 3M Company.

Figure 2C:
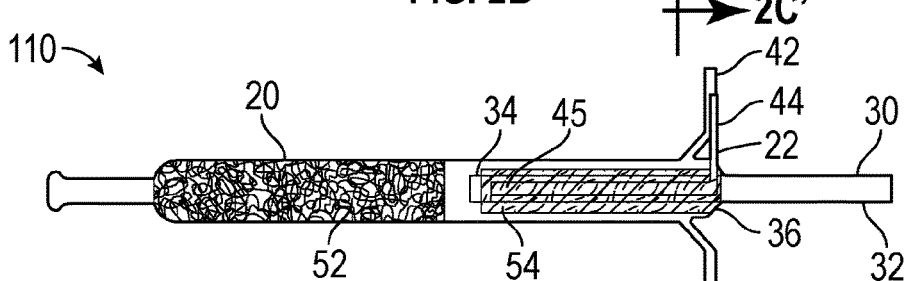
FIG. 2C is a perspective view of an oxy-pyrohydrolysis reactor of the system of FIG. 1, according to another embodiment.
Figure 2C:
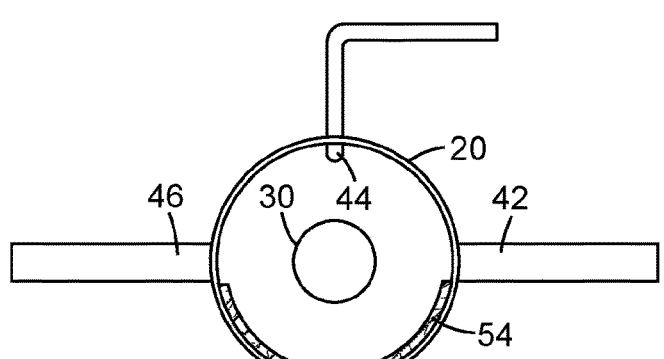

Referring now to FIGS. 2C and 2C', a sheet 54 of ceramic fabric or fiber is disposed on a bottom of the pyrotube 20 adjacent to the first end 22 of the pyrotube. The sheet 54 is positioned between the oxygen inlet 42 and the water inlet 46, and opposite to the flame sensor rod 44. The sheet 54 of ceramic fabric or fiber can help spread and quickly evaporate water from the water inlet 46 along the pyrotube 20. The porosity of the fabric or fiber can spread the water preventing it from pooling. The sheet 54 can extend, for example, about 1/4 to about 1/2 of the length of the pyrotube 20. The sheet 54 can include ceramic fibers or ceramic fabric which is a network of fibers that can be the same or different from the ceramic fibers 52 of FIG. 2A.

Figure 2D:
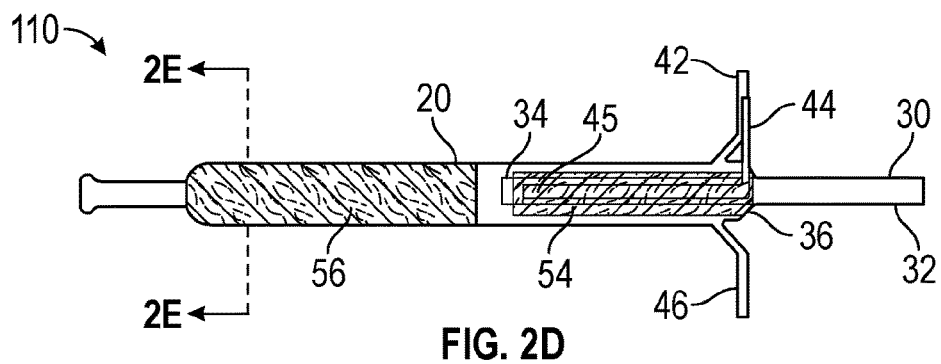
FIG. 2D is a perspective view of an oxy-pyrohydrolysis reactor of the system of FIG. 1, according to another embodiment.
Figure 2E:
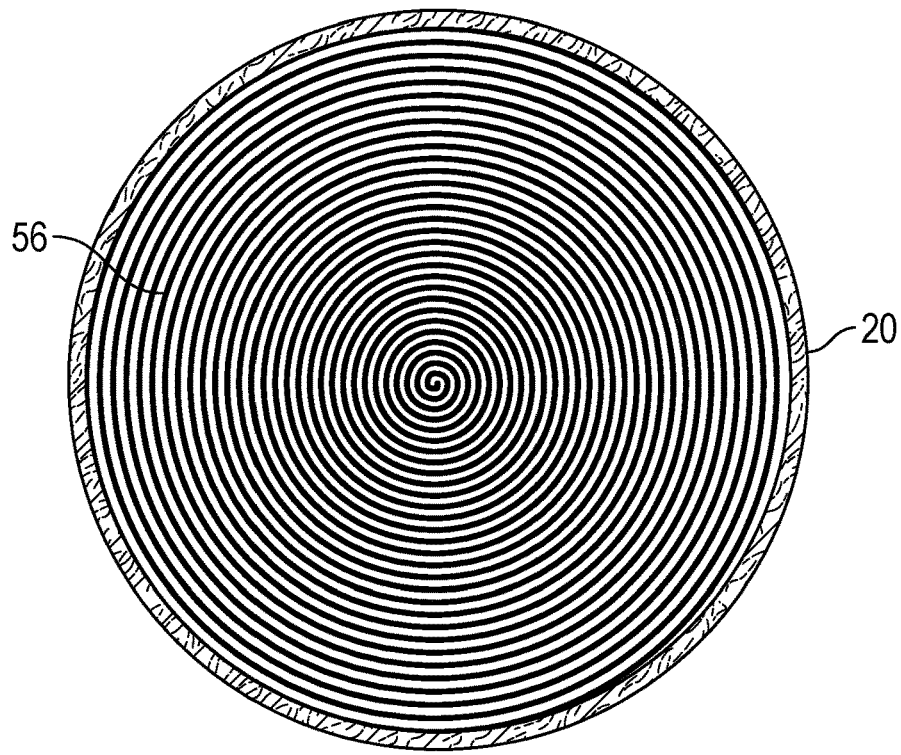
FIG. 2E is a cross sectional view of the oxy-pyrohydrolysis reactor of FIG. 2D along a line 2E-2E.

FIG. 2D illustrates another embodiment of the oxy-pyrohydrolysis reactor 110 where the combustion-enhancing bed includes a roll 56 of ceramic fabric. A cross-sectional view of the oxy-pyrohydrolysis reactor 110 is shown in FIG. 2E. The roll 56 of ceramic fabric is rolled about the central axis of the pyrotube 20 in multiple revolutions. It is to be understood that in some embodiments, the roll of ceramic fabrics can be loosely wound to allow gaps between adjacent revolutions. In some embodiments, spacers can be provided between adjacent revolutions to provide gaps for fluid flow. The roll 56 of ceramic fabric can be a network of fibers that can be the same or different from the ceramic fibers 52 of FIG. 2A.

Figure 2F:
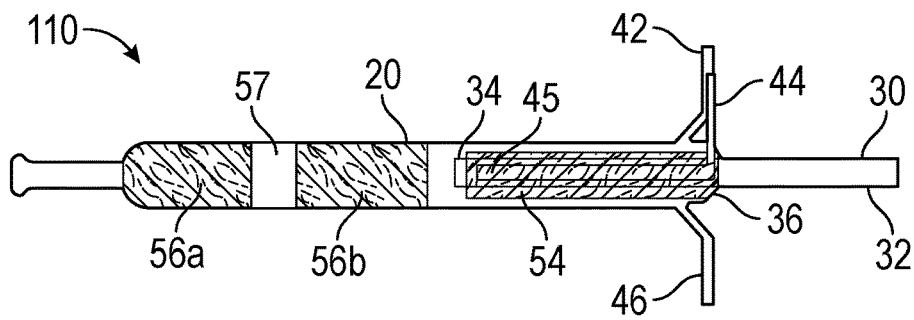
FIG. 2F is a perspective view of an oxy-pyrohydrolysis reactor of the system of FIG. 1, according to another embodiment.
Figure 2G:
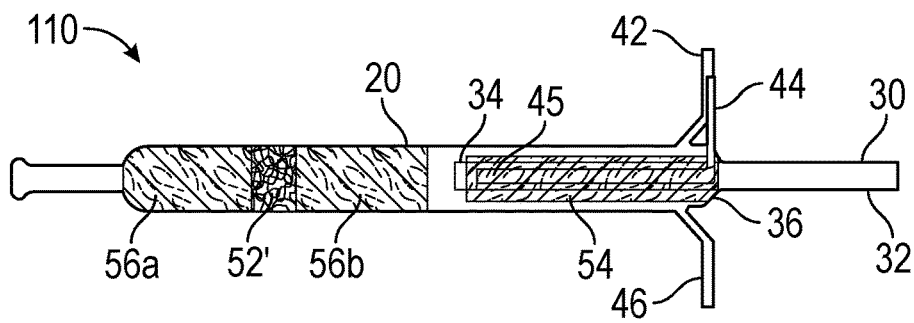
FIG. 2G is a perspective view of an oxy-pyrohydrolysis reactor of the system of FIG. 1, according to another embodiment.
Figure 2H:
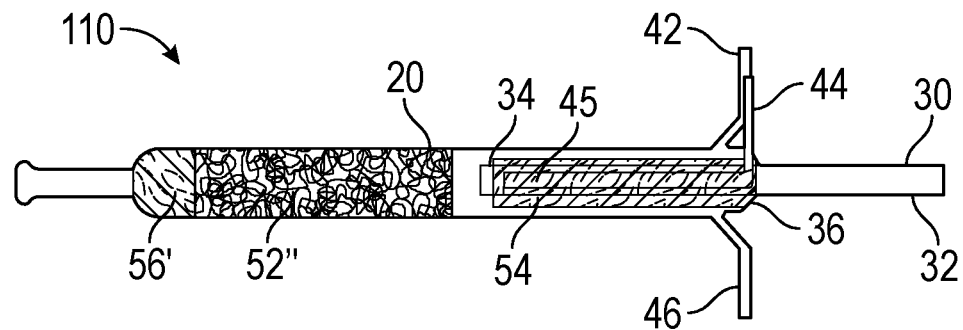
FIG. 2H is a perspective view of an oxy-pyrohydrolysis reactor of the system of FIG. 1, according to another embodiment.

The combustion-enhancing bed can include one or more rolls of ceramic fabric disposed inside the pyrotube 20. As shown in FIG. 2F, a first roll 56a of ceramic fabrics is disposed adjacent to the second end 24, and a second roll 56b of ceramic fabrics is disposed adjacent to the middle of the pyrotube 20. The first and second rolls of ceramic fabrics 56a-b are separated by a gap 57. In the embodiment FIG. 2G, the gap 57 can be filled with a pack of ceramic fibers 52' which may include materials that are the same or different from the pack of ceramic fibers 52 of FIG. 2A. It is to be understood that one or more packs of ceramic fibers and one or more rolls of ceramic fabrics can be combined in any suitable configurations and disposed inside the pyrotube 20 as a combustion-enhancing bed. For example, FIG. 2H illustrates a combustion-enhancing bed including a roll 56' of ceramic fabric and a pack 52" of ceramic fibers disposed in series inside the pyrotube 20.

While not wanting to be bound by theory, it is believed that the combustion-enhancing bed described herein including one or more packs of ceramic fibers or fabrics can enhance sample combustion by slowing down the movement of burning samples toward to the downstream end of the pyrotube. This allows samples to be combusted completely without the formation of black soot which leads to lower the recovery of halogen elements in a downstream analysis. In addition, the packs of ceramic fibers or fabrics can also protect the quartz pyrotube from possible damage by corrosive gases produced in the combustion process. In the presence of the packs of ceramic fibers and/or fabrics, the corrosive gases can be spread or dispersed inside the pyrotube and the chance of etching the pyrotube wall can be reduced. The corrosive gases may include, for example, hydrogen fluoride (HF) which can etch glass, quartz and other materials.

Figure 3A:
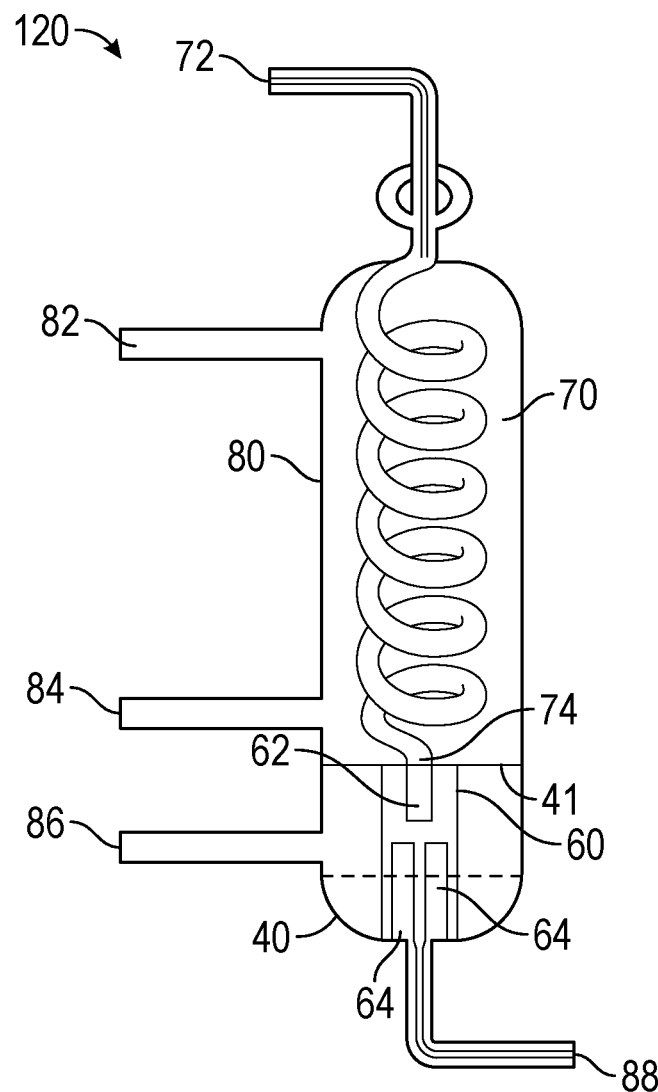
FIG. 3A is a perspective view of a condenser of the system of FIG. 1, according to one embodiment.
Figure 3B:
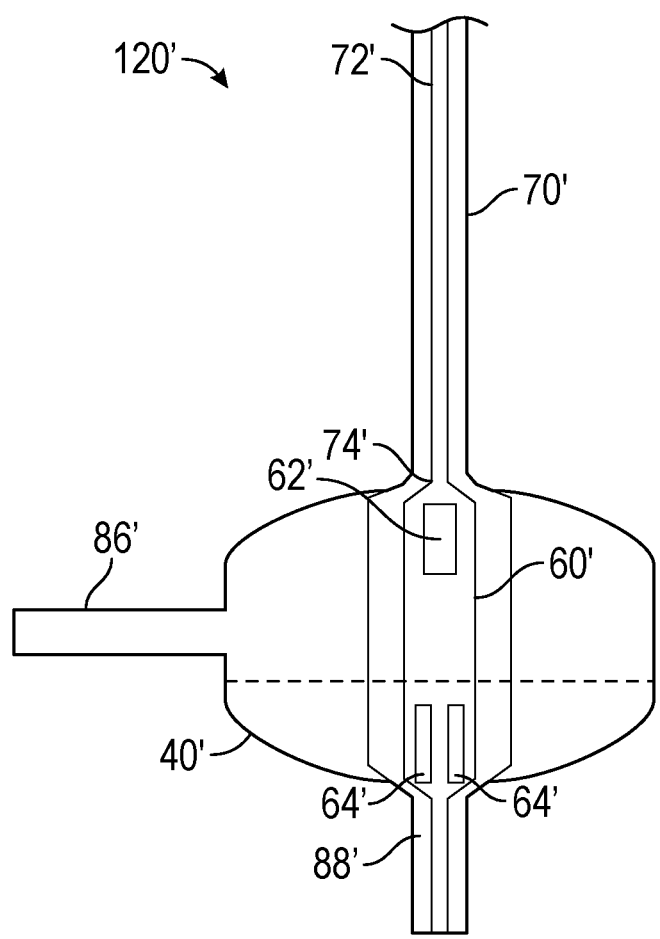
FIG. 3B is a perspective view of a condenser of the system of FIG. 1, according to another embodiment.

FIGS. 3A-B illustrate the condenser 120 (or 120') of FIG. 1, according to various embodiments. As shown in FIG. 3A, the condenser 120 includes a bath tube 80 for running cooling water via an inlet 84 and an outlet 82, a coil 70 for condensing combustion liquid/gas imported from an inlet 72, and a gas-liquid separation chamber 40 located at a downstream position of the bath tube 80 and fluidly separated from the tube 80 by a layer 41. The inlet 72 can, optionally, admit fluid to be mixed with condensed combustion liquid/gas. An inner tube 60 is disposed inside the chamber 40 and fluidly connected to an outlet 74 of the coil 70. A condensed mixture of liquid and gas can be directed, via the outlet 74 of the coil 70 into the inner tube 60. The inner tube 60 has one or more upper vent ports 62 and one or more lower vent ports 64. When the mixture of liquid and gas flow from top to bottom along the inner tube 60, gas can exit through the upper vent ports 62 and can be directed out through an exhaust gas outlet 86, and liquid can exit through the lower vent ports 64 and can be directed through a liquid outlet 88 to a detector.

It is to be understood that combustion products (e.g., gaseous compounds) in optional buffer or rinse water can be condensed by various methods. FIG. 3B illustrates a condenser 120' including a cooling tunnel 70' to condense combustion liquid/gas imported from an inlet 72'. A gas-liquid separation chamber 40' is located at a downstream position and has an inner tube 60' fluidly connected to an outlet 74' of the cooling tunnel 70'. The inner tube 60' has one or more upper vent ports 62' and lower vent ports 64'. When the mixture of liquid and gas flow from top to bottom along the inner tube 60', gas can exit through the upper vent ports 62' and be vented out through an exhaust gas outlet 86', and liquid can exit through the lower vent ports 64' and be directed through a liquid outlet 88' to a detector.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

LIST OF EMBODIMENTS

It is to be understood that any one of embodiments 1-13, 14-32, and 33-37 and can be combined.

Embodiment 1 is an article comprising:
a pyrotube including one or more fluid inlets configured to direct one or more combustion ingredients into the pyrotube; and
a combustion-enhancing bed being disposed inside the pyrotube, the combustion-enhancing bed comprising one or more packs of ceramic fibers or fabrics.

Embodiment 2 is the article of embodiment 1, wherein the pyrotube is made of quartz, glass, ceramic, or platinum.

Embodiment 3 is the article of embodiment 1 or 2, wherein the combustion-enhancing bed comprises randomly packed ceramic fibers.

Embodiment 4 is the article of any one of embodiments 1-3, wherein the combustion-enhancing bed comprises a roll of ceramic fabrics rolling about the axis of the pyrotube.

Embodiment 5 is the article of any one of embodiments 1-4, wherein the ceramic fibers or fabrics comprise alumina-based inorganic oxide fibers or fabrics.

Embodiment 6 is the article of any one of embodiments 1-5, wherein the one or more packs of ceramic fibers or fabrics occupy at least about ⅛ of the length of the pyrotube.

Embodiment 7 is the article of any one of embodiments 1-6 further comprising a sheet of ceramic fabric disposed inside the pyrotube adjacent to the one or more fluid inlets.

Embodiment 8 is the article of any one of embodiments 1-7 further comprising a feed port configured to introduce samples into the pyrotube for combustion.

Embodiment 9 is the article of any one of embodiments 1-8 further comprising a furnace, wherein at least a portion of the pyrotube is positioned inside the furnace.

Embodiment 10 is the article of any one of embodiments 1-9 further comprising a condenser positioned downstream of the pyrotube, and configured to condense combustion products received from the pyrotube.

Embodiment 11 is the article of embodiment 10 further comprising an analyzer functionally connected to the condenser and configured to analyze a composition of the combustion products.

Embodiment 12 is the article of embodiment 10 or 11, wherein the condenser comprises a gas-liquid separation chamber located at a downstream position and configured to separate liquid and gas from a received gas-liquid mixture.

Embodiment 13 is the article of any one of embodiments 10-12, wherein the combustion products include gases by burning solid, liquid, emulsion, or gaseous samples containing fluorine.

Embodiment 14 is a system comprising:
a pyrotube extending along an axis thereof between a first end and a second end opposite the first end;
one or more fluid inlets located at the first end of the pyrotube and configured to direct one or more combustion ingredients into the pyrotube;
a combustion-enhancing bed being disposed inside the pyrotube adjacent to the second end, the combustion-enhancing bed comprising one or more packs of ceramic fibers or fabrics; and
a condenser positioned downstream of the second end of the pyrotube, and configured to condense combustion products received from the pyrotube.

Embodiment 15 is the system of embodiment 14, wherein the pyrotube is made of quartz, glass, ceramic or platinum.

Embodiment 16 is the system of embodiment 14 or 15, wherein the combustion-enhancing bed comprises randomly packed ceramic fibers.

Embodiment 17 is the system of any one of embodiments 14-16, wherein the combustion-enhancing bed comprises a roll of ceramic fabrics rolling about the axis of the pyrotube.

Embodiment 18 is the system of any one of embodiments 14-17, wherein the ceramic fibers or fabrics comprise alumina-based inorganic oxide fibers or fabrics.

Embodiment 19 is the system of embodiment 18, wherein the alumina-based inorganic oxide fibers or fabrics comprise at least 60% by weight of alumina.

Embodiment 20 is the system of embodiment 18 or 19, wherein the alumina-based inorganic oxide fibers or fabrics comprise alpha alumina.

Embodiment 21 is the system of any one of embodiments 18-20, wherein the alumina-based inorganic oxide fibers or fabrics further comprise silicon oxide.

Embodiment 22 is the system of any one of embodiments 18-21, wherein the alumina-based inorganic oxide fibers or fabrics further comprise boron oxide.

Embodiment 23 is the system of any one of embodiments 14-22, wherein the one or more packs of ceramic fibers or fabrics occupies at least about ⅛ of the length of the pyrotube.

Embodiment 24 is the system of any one of embodiments 14-23 further comprising a sheet of ceramic fabric disposed inside the pyrotube adjacent to the first end.

Embodiment 25 is the system of any one of embodiments 14-24 further comprising a feed port adjacent to the first end and configured to introduce samples into the pyrotube for combustion.

Embodiment 26 is the system of embodiment 25, wherein the feed port is a separate tube fluidly sealed to the first end of the pyrotube.

Embodiment 27 is the system of embodiment 25, wherein the feed port is an integral portion of the pyrotube.

Embodiment 28 is the system of any one of embodiments 14-27 further comprising a furnace, wherein at least a portion of the pyrotube is positioned inside the furnace.

Embodiment 29 is the system of any one of embodiments 14-28 further comprising an analyzer functionally connected to the condenser and configured to analyze a composition of the combustion products.

Embodiment 30 is the system of any one of embodiments 14-29, wherein the combustion products include gases by burning solid, liquid or emulsion samples containing fluorine.

Embodiment 31 is the system of any one of embodiments 14-30, wherein the pyrotube has an average diameter of about 10 mm to about 10 cm, and a length of about 10 cm to about 100 cm.

Embodiment 32 is the system of any one of embodiments 14-31, wherein the condenser comprises a gas-liquid separation chamber located at a downstream position and configured to separate liquid and gas from a received gas-liquid mixture.

Embodiment 33 is a method comprising:
providing one or more combustion ingredients and a sample containing fluorine into a pyrotube from a first end thereof, the pyrotube extending along an axis thereof between the first end and a second end opposite the first end, and a combustion-enhancing bed being disposed inside the pyrotube adjacent to the second end, the combustion-enhancing bed comprising one or more packs of ceramic fibers or fabrics;
combusting the sample containing fluorine inside the pyrotube to produce combustion products;
condensing the combustion products by a condenser; and
analyzing a fluorine content of the combustion products.

Embodiment 34 is the method of embodiment 33, wherein the sample is combusted at a temperature of about 1000 to 1100° C.

Embodiment 35 is the method of embodiment 33 or 34, wherein the sample is combusted without formation of black soot inside the pyrotube.

Embodiment 36 is the method of any one of embodiments 33-35, wherein a total fluorine content in the sample is determined.

Embodiment 37 is the method of any one of embodiments 33-26, wherein a total fluorine content in the sample is in the range from about 0.005 wt % to about 35 wt %.

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Unless otherwise noted, all parts, percentages, ratios, etc. in the examples and the rest of the specification are by weight, and all reagents used in the examples were obtained, or are available, from general chemical suppliers such as, for example, Sigma-Aldrich Corp., Saint Louis, Mo., or may be synthesized by conventional methods.

The following abbreviations are used in this section: mL=milliliter, min=minutes, ppm=parts per million, ppb=parts per billion, mm=millimeters, g=grams, mg=milligram.

Oxy-Pyrohydrolysis System

Oxy-pyrohydrolysis systems were set up according to the configuration shown in FIG. 1. Components of the oxy-pyrohydrolysis systems are listed in Table 1 below.

TABLE 1

Equipment List

| Item | Reference to FIG. Numbers | Description |
|---|---|---|
| Sample introduction module | 102 | Used for Examples 1-5. Available under the trade designation "Analytikjena ABD Auto Boat Driver/MMS Multi Matrix Sampler" from Metrohm USA, Riverview, FL. |
| Autosampler | 102 | Used for Example 6. Available under the trade designation "858 Professional Sample Processor - Pump - Injector" from Metrohm USA. |
| Oxy-pyrohydrolysis reactor | 110 | A pyrotube 20 with a combustion-enhancing bed 50 packed with ceramic fiber packing 52. |
| Furnace set | 170 | Available under the trade designation "Analytikjena Combustion Module" from Metrohm USA. |
| Condenser | 120 | A glass condenser made of tubing with an internal diameter of 50 mm containing a coilmade of tubing with an internal diameter of 2 mm. |
| Pump | 104 | A peristaltic pump available under the trade designation "Masterflex C/L 77120-62" from Cole-Parmer, Vernon Hills, IL. |
| Pyrotube | 20 | A pyrotube made of quartz tubing with a 30 mm internal diameter, a first end 22, a second end 24, and a separation between the first and second ends of about 290 mm. |
| Ceramic fiber packing | 52 | About 45 g of ceramic fiber, available under the trade designation "Nextel™ 610 Roving, 20,000 denier" from 3M Company, Maplewood, MN, with individual lengths of from about 50 to about 150 mm, packed to fill the portion of the internal volume of pyrotube extending from the second end 24 to about 145 mm from the second end. |
| Fluoride meter module | 106 | Used for Examples 1-5. A meter module, available under the trade designation "867," equipped with a stirrer, available under the trade designation "801," for agitating sample fluid samples imported to the meter module, a fluoride ion selective electrode, available under the trade designation "6.0502.150," a reference electrode, available under the trade designation "6.0750.100," and a peristaltic pump for providing water rinses of the internal volume of the meter module between measurements, available under the trade designation "843," all from Metrohm USA. |
| Anion Chromatography Module | 106 | Used for Example 6. An ion chromatography module, equipped with an eluent production module available under the trade designation "941," a guard column available under the trade designation "Metrosep A Supp 4/5," an anion separation column available under the trade designation "Metrosep A Supp 5-150," and a conductivity detector available under the trade designation "ProfIC Detector MF," all from Metrohm USA. |

Test Samples

Samples were analyzed using the oxy-pyrohydrolysis system described above. The test samples are listed in Table 2 below.

TABLE 2

Test Samples

| Material | Description |
|---|---|
| C8 Fluorinated Compound | Ammonium pentadecafluorooctanoate, commercially available from Sigma-Aldrich Corp., Saint Louis, MO. |
| C4 Fluorinated Compound | Potassium perfluorobutane sulfonate commercially available from Kingchem LLC, Allendale, NJ. |
| Potassium nonafluoro-1-butanesulfonate | 98% purity, available from Sigma-Aldrich Corp. |
| 3-chloro-1-propanol | Available from Sigma-Aldrich Corp. |
| Fluoride Standard | A 100 ppm as $F^-$ standard, available under the trade designation "ORION® 940907" from VWR, Radnor, PA. |
| Buffer | Available under the trade designation "ORION® TISAB II" from VWR, Radnor, PA. |

TABLE 2-continued

Test Samples

| Material | Description |
|---|---|
| NaCO$_3$ | 99.99% purity, available from Sigma-Aldrich Company. |
| NaHCO$_3$ | 99.99% purity, available from Sigma-Aldrich Company. |
| ANIONS Mix3 | 100 ppm Anions standard solution, available under the trade designation "REAIC1035" from Metrohm USA. |
| Water | De-ionized water |

Average Recovery

The term "average recovery," is used in this section as the mean of a concentration of an analyte determined in replicate measurements of a sample, divided by the known concentration in the sample, multiplied by 100, and reported as a percentage. When the mean is reported with a standard deviation, the value of the standard deviation, divided by the known concentration in the sample, and multiplied by 100, is also reported as a percentage. For example, if the mean and standard deviation for replicate measurements of the concentration of the analyte fluorine in a sample is 950±10 ppm, and the known concentration of the analyte fluorine in the sample is 1000 ppm, the average recovery would be calculated as [(950 ppm/1000 ppm)×100]±[(10 ppm/1000 ppm)×100], or 95%±1%.

Example 1 (EX-1) Recovery Using C8 Fluorinated Compound

In Example 1, water was supplied to a fluid inlet of the pyrotube at a rate of 0.6 mL/min. Oxygen was supplied to the pyrotube at a rate of 300 mL/min through the other fluid inlet and 200 mL/min through the sample inlet. The pyrotube was heated by the furnace set to a temperature of about 1050° C. A solution of C8 fluorinated compound that was diluted to a concentration of 1000 ppm fluorine was prepared in water. For each replicate determination, a 100 mg sample of solution was placed in a ceramic boat by the autosampler of the sample introduction module and introduced by the sample introduction module into the pyrotube a controlled rate. Pyrolysis gases produced by oxy-pyrohydrolysis of the sample flowed through the combustion-enhancing bed, out of the pyrotube, and into the coil of the condenser. Also flowing into the coil was buffer, at a flow rate of 0.6 mL/min. Cooling water, chilled to a temperature of 15° C., was pumped through the bath tube. The condensate from the pyrolysis gases mixed with buffer and was transferred from the liquid outlet to the fluoride meter module. Between determinations, the internal volume of the fluoride meter module was rinsed with water pumped by the pump. Fluoride concentration in the fluid pumped to the meter module was measured and converted to concentration of fluorine in the sample with the use of calibration curves constructed from measurements of dilutions of fluoride standard of known fluoride concentrations. The replicate determinations of fluorine, the mean, the standard deviation and average recovery for 14 replicate determinations are reported in Table 3 below.

TABLE 3

Results for EX-1

| Replicate | EX-1 Measured Fluorine (ppm) |
|---|---|
| 1 | 1026 |
| 2 | 1037 |
| 3 | 941 |
| 4 | 1006 |
| 5 | 1031 |
| 6 | 915 |
| 7 | 985 |
| 8 | 1026 |
| 9 | 1054 |
| 10 | 1022 |
| 11 | 1019 |
| 12 | 934 |
| 13 | 1026 |
| 14 | 1037 |
| Mean ± Standard Deviation | 1000 ± 44 |
| Known Concentration | 1000 |
| Average Recovery | 100% ± 4.4% |

Example 2 (EX-2) Recovery Using C4 Fluorinated Compound

For EX-2, the procedure described for EX-1 was followed, except that the sample analyzed was a solution of C4 fluorinated compound diluted to a fluorine concentration of 50 ppm and there were three replicate determinations made. The individual results, the mean, the standard deviation and average recovery for three replicate determinations are reported in Table 4 below.

TABLE 4

Results for EX-2, EX-3, EX-4, and EX-5

| Replicate | EX-2 Measured Fluorine (ppm) 50 ppm Solution | EX-3 Measured Fluorine (ppm) 100 ppm Solution | EX-4 Measured Fluorine (ppm) 1000 ppm Solution | EX-5 Measured Fluorine (%) 1.529% Solution |
|---|---|---|---|---|
| 1 | 57 | 111 | 1003 | 1.501 |
| 2 | 59 | 116 | 1065 | 1.555 |
| 3 | 48 | 113 | 1016 | 1.491 |
| 4 | NM | 114 | 821 | 1.465 |
| 5 | NM | 105 | 903 | 1.506 |
| 6 | NM | 105 | 891 | 1.597 |
| 7 | NM | 106 | 1107 | 1.589 |
| 8 | NM | 105 | 1091 | 1.613 |
| 9 | NM | 115 | 1040 | 1.524 |

TABLE 4-continued

Results for EX-2, EX-3, EX-4, and EX-5

| Replicate | EX-2 Measured Fluorine (ppm) 50 ppm Solution | EX-3 Measured Fluorine (ppm) 100 ppm Solution | EX-4 Measured Fluorine (ppm) 1000 ppm Solution | EX-5 Measured Fluorine (%) 1.529% Solution |
|---|---|---|---|---|
| 10 | NM | 108 | 1053 | 1.524 |
| 11 | NM | 109 | 990 | 1.552 |
| 12 | NM | 111 | 1011 | 1.475 |
| 13 | NM | NM | 1040 | 1.539 |
| 14 | NM | NM | 1064 | 1.419 |
| 15 | NM | NM | 946 | 1.560 |
| 16 | NM | NM | 937 | 1.556 |
| 17 | NM | NM | 987 | 1.534 |
| 18 | NM | NM | 1002 | 1.498 |
| 19 | NM | NM | 995 | NM |
| 20 | NM | NM | 971 | NM |
| 21 | NM | NM | 984 | NM |
| 22 | NM | NM | 1041 | NM |
| 23 | NM | NM | 1098 | NM |
| 24 | NM | NM | 969 | NM |
| Mean ± Standard Deviation | 55 ± 5 | 100 ± 4 | 1001 ± 67 | 1.528 ± 0.0478 |
| Known Concentration | 50 | 100 | 1000 | 1.529 |
| Average Recovery | 110% ± 10% | 100% ± 4% | 100% ± 6.7% | 100% ± 3.1% |

NM = Not Measured

Example 3 (EX-3) Recovery Using C4 Fluorinated Compound

For EX-3, the procedure described for EX-1 was followed, except that the sample was diluted to a fluorine concentration of 100 ppm and 12 replicate determinations were made. The individual results, the mean, the standard deviation and average recovery for 12 replicate determinations are reported in Table 4.

Example 4 (EX-4) Recovery Using C4 Fluorinated Compound

For EX-4, the procedure described for EX-2 was followed, except that the sample was diluted to a fluorine concentration of 1000 ppm and 24 replicate determinations were made. The individual results, the mean, the standard deviation and average recovery for 24 replicate determinations are reported in Table 4.

Example 5 (EX-5) Recovery Using C4 Fluorinated Compound

For EX-5, the procedure described for EX-2 was followed, except that the sample was diluted to a known fluorine concentration of 1.529% and 18 replicate determinations were made. The individual results, the mean, the standard deviation and average recovery for 18 replicate determinations are reported in Table 4.

Example 6 (EX-6) Recovery Using C4 Fluorinated Compound

In Example 6, the pyrotube was heated by the furnace set to a temperature of about 1050° C. A solution of potassium nonafluoro-1-butanesulfonate that was diluted to a concentration of 1000 ppb fluorine was prepared in water. This solution was serially diluted to provide the samples of concentration indicated in Table 5 below. Replicate determinations of fluorine in the samples were made. For each replicate determination, the autosampler was used to deliver 3.50 mL of the sample solution into the pyrotube at a flow rate of 0.3 mL/min. Pyrolysis gases produced by oxy-pyrohydrolysis of the sample flowed through the combustion-enhancing bed, out of the pyrotube, and into the coil of the condenser. Cooling water, chilled to a temperature of 15° C., was pumped through the bath tube. The condensate from the pyrolysis gases was transferred from the liquid outlet to the anion chromatography module. Between determinations, the internal volume of the anion chromatography module injection port was rinsed with water pumped by the pump. Fluoride concentration in the fluid pumped to the anion chromatography module was measured and converted to concentration of fluorine in the sample with the use of calibration curves constructed from measurements of fluoride in serially diluted ANIONS Mix3 standard in the range from 1 ppb to 100 ppb. The ion chromatography eluent was a solution of 3.2 mM $NaCO_3$ and 1.0 $NaHCO_3$ flowing at a rate of 0.7 mL/min. The column oven temperature was 40° C. For each sample, the number of replicate determinations, the mean, the standard deviation and average recovery are reported in Table 5 below.

TABLE 5

Results for EX-6

| Sample Concentration (ppb) | Number of Replicate Determinations | Mean ± Standard Deviation (ppb) | Average Recovery (%) |
|---|---|---|---|
| 0 | 5 | 3.5 ± 0.07 | NA |
| 10 | 5 | 11 ± 0.3 | 110.0 ± 3 |
| 20 | 5 | 20 ± 0.6 | 100.0 ± 3 |
| 40 | 5 | 38 ± 0.6 | 95.0 ± 2 |
| 50 | 6 | 53 ± 0.9 | 106.0 ± 2 |
| 60 | 5 | 58 ± 0.3 | 96.7 ± 2 |
| 80 | 5 | 76 ± 1.3 | 95.0 ± 1.6 |
| 100 | 17 | 95 ± 3.2 | 95.0 ± 3.2 |
| 250 | 6 | 230 ± 5.1 | 92.0 ± 2.0 |
| 500 | 12 | 479 ± 11.2 | 95.8 ± 2.24 |
| 1000 | 12 | 1052 ± 20.5 | 105.2 ± 2.1 |

N/A = Not Applicable

Example 7 (EX-7) Recovery Using Chlorinated Compound

In Example 7, the pyrotube was heated by the furnace set to a temperature of about 1050° C. A solution of 3-chloro-1-propanol that was diluted to a concentration of 1000 ppb fluorine was prepared in water. This solution was serially diluted to provide the samples of concentration indicated in Table 6 below. Replicate determinations of chlorine in the samples were made. For each replicate determination, the autosampler was used to deliver 3.50 mL of the sample solution into the pyrotube at a flow rate of 0.3 mL/min. Pyrolysis gases produced by oxy-pyrohydrolysis of the sample flowed through the combustion-enhancing bed, out of the pyrotube, and into the coil of the condenser. Cooling water, chilled to a temperature of 15° C., was pumped through the bath tube. The condensate from the pyrolysis gases was transferred from the liquid outlet to the anion chromatography module. Between determinations, the internal volume of the anion chromatography module injection port was rinsed with water pumped by the pump. Chloride concentration in the fluid pumped to the anion chromatography module was measured and converted to concentration of chlorine in the sample with the use of calibration curves constructed from measurements of chloride in serially diluted ANIONS Mix3 standard in the range from 1 ppb to 100 ppb. The ion chromatography eluent was a solution of 3.2 mM $NaCO_3$ and 1.0 $NaHCO_3$ flowing at a rate of 0.7 mL/min. The column oven temperature was 40° C. For each sample, the number of replicate determinations, the mean, the standard deviation and average recovery are reported in Table 6 below.

TABLE 6

Results for EX-7

| Sample Concentration (ppb) | Number of Replicate Determinations | Mean ± Standard Deviation (ppb) | Average Recovery (%) |
|---|---|---|---|
| 0 | 5 | 2.0 ± 0.18 | NA |
| 10 | 5 | 10 ± 0.1 | 100 ± 1 |
| 20 | 5 | 19 ± 0.5 | 94 ± 3 |
| 40 | 4 | 39 ± 0.6 | 99 ± 1 |
| 60 | 5 | 59 ± 2.1 | 99 ± 3.5 |
| 80 | 5 | 78 ± 1.8 | 98 ± 2.2 |
| 100 | 5 | 94 ± 2.3 | 94 ± 2.2 |

N/A = Not Applicable

Foreseeable modifications and alterations of this disclosure will be apparent to those skilled in the art without departing from the scope and spirit of this disclosure. This disclosure should not be restricted to the embodiments that are set forth in this application for illustrative purposes.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure.

Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about."

Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. An article comprising:
    a pyrotube including one or more fluid inlets configured to direct one or more combustion ingredients into the pyrotube, wherein the one or more fluid inlets include a water inlet and an oxygen inlet disposed on opposite sides of the pyrotube;
    a sheet of ceramic fabric disposed on a bottom surface of the pyrotube adjacent to and lower than the water inlet and the oxygen inlet, configured to spread and evaporate water from the water inlet along the pyrotube; and
    a combustion-enhancing bed being disposed inside the pyrotube and downstream of the sheet of ceramic fabric, the combustion-enhancing bed comprising one or more packs of ceramic fibers or fabrics.

2. The article of claim 1, wherein the combustion-enhancing bed comprises randomly packed ceramic fibers.

3. The article of claim 1, wherein the combustion-enhancing bed comprises a roll of ceramic fabrics rolling about the axis of the pyrotube.

4. The article of claim 1, wherein the ceramic fibers or fabrics comprise alumina-based inorganic oxide fibers or fabrics.

5. The article of claim 1 further comprising a furnace, wherein at least a portion of the pyrotube is positioned inside the furnace.

6. The article of claim 1 further comprising a condenser positioned downstream of the pyrotube, and configured to condense combustion products received from the pyrotube.

7. The article of claim 6 further comprising an analyzer functionally connected to the condenser and configured to analyze a composition of the combustion products.

8. The article of claim 6, wherein the condenser comprises a gas-liquid separation chamber located at a downstream position and configured to separate liquid and gas from a received gas-liquid mixture.

9. A system comprising:
    a pyrotube extending along an axis thereof between a first end and a second end opposite the first end;
    one or more fluid inlets located at the first end of the pyrotube and configured to direct one or more combustion ingredients into the pyrotube, wherein the one or more fluid inlets include a water inlet and an oxygen inlet disposed on opposite sides of the pyrotube;

a sheet of ceramic fabric disposed on a bottom surface of the pyrotube adjacent to and lower than the water inlet and the oxygen inlet, configured to spread and evaporate water from the water inlet along the pyrotube;

a combustion-enhancing bed being disposed inside the pyrotube downstream of the sheet of ceramic fabric and adjacent to the second end, the combustion-enhancing bed comprising one or more packs of ceramic fibers or fabrics; and a condenser positioned downstream of the second end of the pyrotube, and configured to condense combustion products received from the pyrotube.

10. The system of claim 9, wherein the pyrotube is made of quartz, glass, ceramic or platinum.

11. The system of claim 9, wherein the combustion-enhancing bed comprises randomly packed ceramic fibers.

12. The system of claim 9, wherein the combustion-enhancing bed comprises a roll of ceramic fabrics rolling about the axis of the pyrotube.

13. The system of claim 9, wherein the ceramic fibers or fabrics comprise alumina-based inorganic oxide fibers or fabrics.

14. The system of claim 13, wherein the alumina-based inorganic oxide fibers or fabrics comprise at least 60% by weight of alumina.

15. A method comprising:

providing one or more combustion ingredients, and a sample into a pyrotube from a first end thereof, the sample containing one or more halogen elements, the pyrotube extending along an axis thereof between the first end and a second end opposite the first end, one or more fluid inlets located at the first end of the pyrotube and configured to direct one or more combustion ingredients into the pyrotube, the one or more fluid inlets include a water inlet and an oxygen inlet, a sheet of ceramic fabric disposed on a bottom surface of the pyrotube adjacent to and lower than the water inlet and the oxygen inlet, configured to spread and evaporate water from the water inlet along the pyrotube, and a combustion-enhancing bed being disposed inside the pyrotube downstream of the sheet of ceramic fabric and adjacent to the second end, the combustion-enhancing bed comprising one or more packs of ceramic fibers or fabrics; and combusting the sample inside the pyrotube to produce combustion products.

16. The method of claim 15, wherein the sample is combusted at a temperature of about 1000° C. to about 1100° C.

17. The method of claim 15 further comprising condensing the combustion products by a condenser.

18. The method of claim 15 further comprising analyzing the combustion products to determine a total fluorine content in the sample.

* * * * *